United States Patent [19]

Schulz

[11] Patent Number: 4,761,558

[45] Date of Patent: Aug. 2, 1988

[54] APPARATUS FOR VIEWING A FOIL IRRADIATED IN THE COURSE OF NEUTRON RADIOGRAPHY

[75] Inventor: Wolfgang Schulz, Wunstorf, Fed. Rep. of Germany

[73] Assignee: Brown Boveri Reaktor GmbH, Mannheim, Fed. Rep. of Germany

[21] Appl. No.: 912,929

[22] Filed: Sep. 26, 1986

[30] Foreign Application Priority Data

Sep. 28, 1985 [DE] Fed. Rep. of Germany ....... 3534759

[51] Int. Cl.⁴ ............................ G01T 3/00; G01T 5/02
[52] U.S. Cl. ................................. 250/485.1; 250/390; 250/472.1
[58] Field of Search ............... 250/485.1, 472.1, 473.1, 250/390 B, 390 A

[56] References Cited

PUBLICATIONS

Khan, "Semi-Automatic Scanning of Tracks in Plastics", Radiation Effects, 8 (1-2), 1971, pp. 135-138, Glasgow, Scotland.

Heinecke et al., "Particle Discrimination by an Automatic Scanner for Nuclear Emulsion Plates", Nucl. Instr. and Methods 133 (2), Mar. 1, 1976, pp. 283-292.

Primary Examiner—Carolyn E. Fields
Attorney, Agent, or Firm—Herbert L. Lerner; Laurence A. Greenberg

[57] ABSTRACT

An apparatus for viewing a foil irradiated in the course of neutron radiography, the foil having nuclear tracks being visible after etching under the action of light, includes a completely enclosed housing having a first surface with an opening formed therein for receiving an etched foil, a second surface opposite the opening, a black coating disposed on the second surface, and at least one light source disposed between the black coated second surface and the opening for transmitting light rays striking the foil in the opening at an angle deviating from the normal.

5 Claims, 1 Drawing Sheet

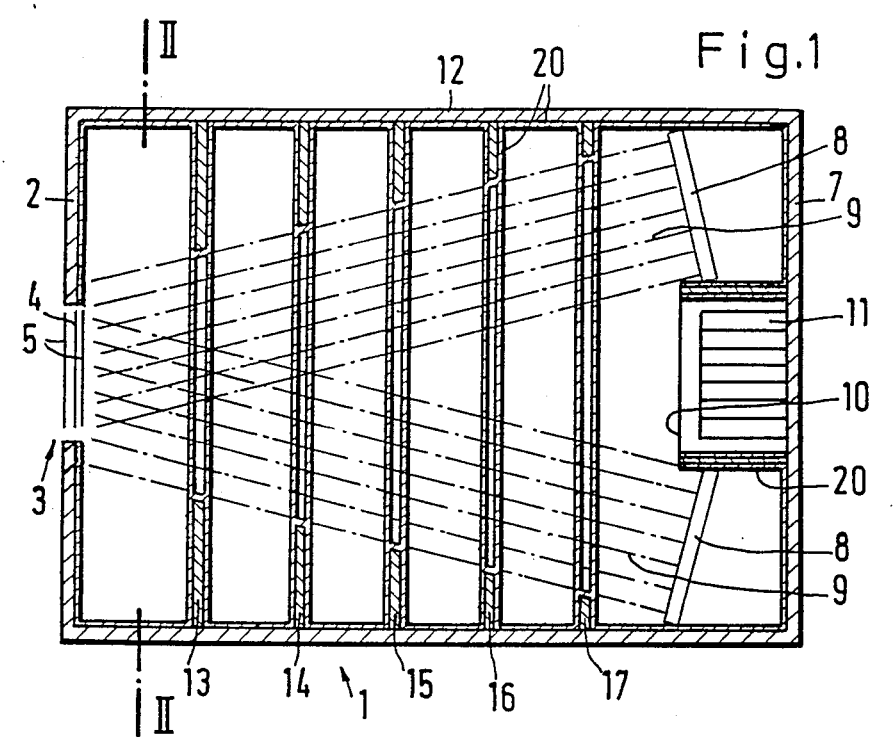
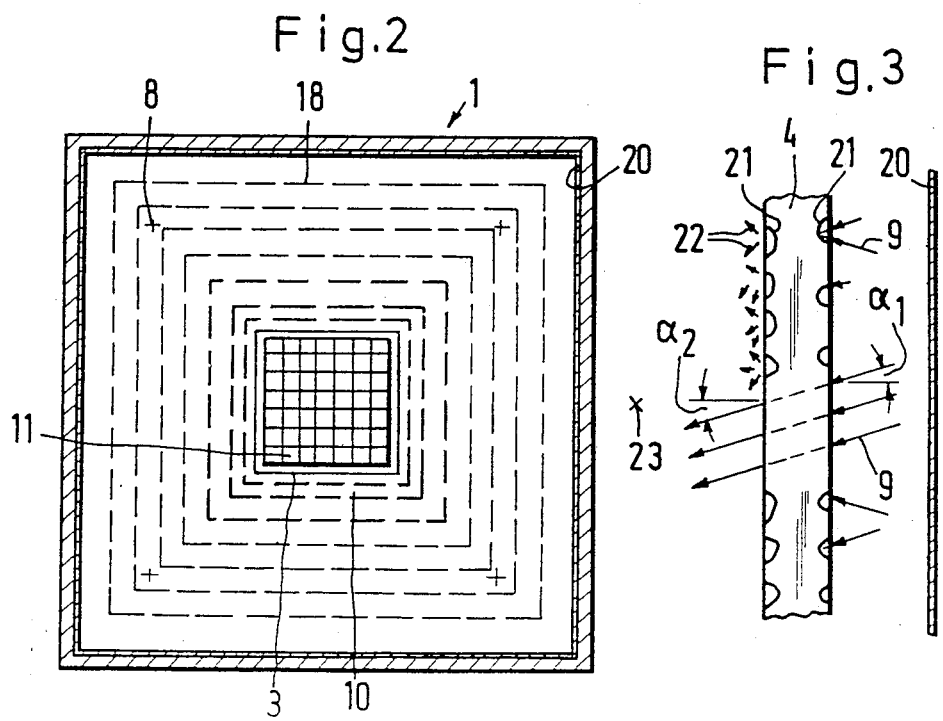

APPARATUS FOR VIEWING A FOIL IRRADIATED IN THE COURSE OF NEUTRON RADIOGRAPHY

The invention relates to an apparatus for viewing and reproducing a foil irradiated in the course of neutron radioagraphy, having nuclear tracks being visible under the action of light after slight etching.

The nondestructive testing of materials, especially radioactive objects, by means of neutron radiography, is known from the journal Materialprufung (Material Testing) 18 (1976) No. 5, pages 171 to 175. The publication describes various methods in addition to direct neutron radiography with track detectors. In direct neutron radiogaphy, nuclear tracks which become visible as etch tracks in a developer bath, are formed on a film foil subordinated to the irradiated object. The etch tracks are differ in diameter, depth and frequency as a function of the irradiated object and of the radiation time and intensity. It is generally known how to make the etch tracks visible under the action of light. In order to obtain a picture capable of revealing information, it has heretofore been necessary to use long exposure times or strong and cost-intensive neutron source equipment, because weak etch track pictures with too low an etch track density lead to a contrastless picture which is difficult or impossible to interpret.

It is accordingly an object of the invention to provide an apparatus for viewing a foil irradiated in the course of neutron radiography, which overcomes the hereinafore-mentioned disadvantages of the heretofore-known devices of this general type and by means of which lightly etched nuclear track pictures with a low etch track frequency can also be interpreted completely and with good contrast.

With the foregoing and other objects in view there is provided, in accordance with the invention, an apparatus for viewing a foil irradiated in the course of neutron radiography, the foil having nuclear tracks or traces being visible after slight etching under the action of light, comprising a completely enclosed housing having a first surface with an opening formed therein for receiving an etched foil, a second surface opposite the opening, an extremely black, non-relfective coating disposed on the second surface, and at least one light source disposed between the black coated second surface and the opening for transmitting light rays striking the foil in the opening at an angle deviating from the normal. The film areas not containing etch tracks appear dark against the black background because the light rays are not being reflected.

However, if the film foil does contain etch tracks, different brightnesses will appear on the film as a function of the diameter, the depth and especially the etch track density. The contrast intensification achieved in this way produces exactly interpretable pictures even with a low etch track frequency. A reduction of the radiation time by a multiple when preparing the film foil must be viewed as an additional advantage.

In accordance with another feature of the invention, the housing includes remaining inner surfaces other than the first and second surfaces and the opening defines a plane for the foil, and including at least one web plate parallel to the plane for the foil having a surface with an aperture formed therein through which the light rays pass, the black coating being disposed on the surface of the web plate as well as on the remaining inner surfaces of the housing. To a great extent, this avoids reflection and scatter effects on the surface of the housing opposite the opening for receiving the foil.

In accordance with a further feature of the invention, the at least one web plate is in the form of a plurality of web plates having apertures formed therein defining edges of the apertures, the apertures being continuously smaller as viewed in direction toward the opening and the edges of the apertures being parallel to the light rays.

In accordance with an added feature of the invention, the opening has an unobstructed region of a given size, and including a compartment, well or shaft protruding from the second surface having outer surfaces and inner surfaces defining an unobstructed region formed therein being larger than the given unobstructed region, the compartment having ends facing away from the second surface being closer to the opening than the light sources, and the black coating being disposed on the inner and outer surfaces of the compartment. This is provided for contrast enhancement or for the differentiation of even finer contrasts as a function of the shape and frequency of the etch track distribution.

In accordance with a concomitant feature of the invention, the compartment has an upper edge, and including a multiplicity of cells, second wells or shaft disposed inside the compartment or first well or shaft having walls with inner and outer sufaces ending below the upper edge of the compartment, and the black coating being disposed on the inner and outer surfaces of the cells or second wells or shafts. This is done in order to achieve a still deeper darkening of the background and thus a further contrast intensification.

The combination of the compartment and cell or two well construction is to be dimensioned in such a way that stray radiation stemming from the light source does not render a grid raster of the many small cells or wells recognizable and that the housing area enclosed by the cells appears homogeneous and extremely black.

Other features which are considered as characteristic for the invention are set forth in the appended claims.

Although the invention is illustrated and described herein as embodied in an apparatus for viewing a foil irradiated in the course of neutron radiography, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 1 is a diagrammatic longitudinal sectional view of the apparatus according to the invention;

FIG. 2 is a cross-sectional view taken along the line II—II in FIG. 1, in the direction of the arrows; and FIG. 3 is a fragmentary view of the foil shown in FIG. 1 on a larger scale.

Referring now to the figures of the drawings in detail and first, particularly, to FIG. 1 thereof, there is seen a longitudinal section of the apparatus showing a cuboid or parallelepiped housing 1. An opening 3 for receiving a film foil 4 containing etch tracks is formed in the center of a first surface 2 of the housing 1. The foil is clamped between two thin, plane-parallel transparent glass panes 5 held in the opening 3 by means of a nonillustrated frame. The film foil is positioned relative to the opening in such a way that it is disposed in the center of the surface 2. Nuclear tracks have been made visible on the foil by the etch tracks applied in the course of neutron radiography. Four light sources 8 which are positioned between the first surface 2 and an opposite second surface 7 in a symmetrical arrangement, transmit light rays 9 which strike the foil 4 at an angle deviating from the normal. The paths of the light rays 9 from the sources 8 are aligned so that they strike the foil 4 which is clamped between the glass panes 5 with a plane-parallel radiant energy which depends on direction and distance and which attains plane a uniformity of luminous intensity distribution of ≦2.5% at the plane of the foil.

Jutting out from the surface 7 opposite the opening 3 is a compartment, well or shaft 10 having free ends which are nearer the opening 3 than the light sources 8. The size of the inside width of compartment 10 is at least that of the opening 3. As may also be seen from FIG. 2, a multiplicity of cells, wells or shafts 11, filling the cross-sectional area of the compartment 10 and disposed in chess board fashion, are disposed inside the compartment 10. The walls of the cells 11 end below the upper edge of compartment 10 accommodating the cells. Five web plates, straps or ribs 13 to 17 which are mutually equidistant, as viewed in axial direction of the housing 1, jut out from the sidewalls 12 of housing 1. All of the web plates are disposed between the opening 3 and the light sources 8. It becomes clear in connection with FIG. 2 that the web plates each have an aperture 18 with square cross sections, disposed symmetrical to the longitudinal axis of housing 1. While the web plate 17 located next to the light sources 8 has the largest aperture, the web plate 13 associated with the opening 3 has the smallest aperture. The apertures of the web plates 14, 15 and 16 inbetween are dimensioned so as to continuously increase in the direction toward the light source 8. An imaginary line interconnecting the edges of the apertures would run parallel to the rays 9 of the light source 8. All of the inner surfaces of the housing 1, including the web plates 13 through 17, the compartment 10 and of the cells 11 disposed therein are provided with an extremely black and non-reflective coating 20.

The operation of the apparatus is described below. Etch tracks of different diameters and depths are disposed on a developed nuclear track film foil 4. The foil 4, clamped between the glass panes 5, is struck by light flux at a given angle α relative to the perpendicular foil plane. The light flux has a uniform luminous intensity distribution on the image plane at a given intensity. When a radiant energy strikes a foil surface area not containing etch tracks, the light flux is conducted through the foil with little deflection so that the brightness of the foil surface area is determined essentially by the degree of background blackness. The formation of a deep black background is provided by the compartment and cell combination opposite the opening. The black coating 20 on the remaining inner surfaces of the housing serve the purpose of preventing reflections and stray light effects which would have an influence on the contrast and the exact reproduction of the etch track picture. However, if the light flux hits a foil surface area containing etch tracks, the light flux will be dispersed in diverse directions at the angle so that different brightnesses will appear on the film surface, according to the frequency of the etch tracks, depending only insignificantly upon the background and being caused by diffuse dispersion of the light. Thus, if an observer station is located in front of the film foil plane, the partial foil film areas containing no etch tracks or only a few etch tracks are determined by the structure of the apparatus and in particular by the degree of blackness of that part of the rear wall of the housing located behind the foil plane. On the other hand, the brightness of the partial foil film areas containing etch tracks of greater frequency (density) depends essentially on the frequency, size and shape of the etch tracks or on the luminous intensity (distribution) of the radiant energy striking the film. Thus, the developed neutron radiographic films experience a significant contrast intensification and good visual readability through the apparatus according to the invention.

FIG. 3 shows a portion of the foil 4 on a larger scale. The deep black background is again given reference numeral 20. The light rays 9 striking a foil area without etch tracks are only deflected insignificantly so that an angle $\alpha_1$ almost equal an angle $\alpha_2$. On the other hand, the light rays 9 hitting etch tracks 21 lead to a diffuse dispersion of the light, as indicated by arrows 22. As viewed from an observation position 23, a picture rich in contrast is presented, from which informative photos can be made directly.

The foregoing is a description corresponding in substance to German Application P No. 35 34 759.7, dated Sept. 28, 1985, the International priority of which is being claimed for the instant application, and which is hereby made part of this application. Any material discrepancies between the foregoing specification and the aforementioned corresponding German application are to be resolved in favor of the latter.

I claim:

1. Apparatus for viewing a foil irradiated in the course of neutron radiography, the foil having nuclear tracks being visible after etching under the action of light, comprising a completely enclosed housing having a first surface with means defining an opening therein for receiving an etched foil, a second surface opposite said opening, a black coating disposed on said second surface, and at least one light source disposed in said housing between the black coated second surface and said opening for transmitting light rays striking the foil in said opening at an angle deviating from the normal.

2. Apparatus according to claim 1, wherein said housing includes remaining inner surfaces other than said first and second surfaces and said opening defines a plane for the foil, and including at least one web plate parallel to said plane for said foil having a surface with an aperture formed therein through which the light rays pass, said black coating being disposed on said surface of said at least one web plate as well as on said remaining inner surfaces of said housing.

3. Apparatus according to claim 2, wherein said at least one web plate is in the form of a plurality of web plates having apertures formed therein defining edges of said apertures, said apertures being continuously smaller as viewed in direction toward said opening and said edges of said apertures being parallel to the light rays.

4. Apparatus for viewing a foil irradiated in the course of neutron radiography, the foil having nuclear tracks being visible after etching under the action of light, comprising a completely enclosed housing having a first surface with means defining an opening therein with a given unobstructed region of a given size for receiving an etched foil, a second surface opposite said opening, a black coating disposed on said second surface, at least one light source disposed between the black coated second surface and said opening for transmitting light rays striking the foil in said opening at an angle deviating from the normal, and a compartment protruding from said second surface having outer surfaces and inner surfaces defining an unobstructed region formed therein being larger than said given unobstructed region, said compartment having ends facing away from said second surface being closer to said opening than said at least one light source, and said black coating being disposed on said inner and outer surfaces of said compartment.

5. Apparatus according to claim 4, wherein said compartment has an upper edge, and including a multiplicity of cells disposed inside said compartment having walls with inner and outer surfaces ending below said upper edge of said compartment, and said black coating being disposed on said inner and outer surfaces of said cells.

* * * * *